(12) United States Patent
Edgar et al.

(10) Patent No.: US 12,011,561 B2
(45) Date of Patent: Jun. 18, 2024

(54) SYSTEM AND METHOD FOR SELECTIVE APPLICATION OF COSMETIC COMPOSITION TO IMPART UNDEREYE BRIGHTENING

(71) Applicant: JOHNSON & JOHNSON CONSUMER INC., Skillman, NJ (US)

(72) Inventors: Albert Durr Edgar, Austin, TX (US); Laura Higgins, Boston, MA (US)

(73) Assignee: JOHNSON & JOHNSON CONSUMER INC., Skillman, NJ (US)

( * ) Notice: Subject to any disclaimer, the term of this patent is extended or adjusted under 35 U.S.C. 154(b) by 80 days.

(21) Appl. No.: 17/444,136

(22) Filed: Jul. 30, 2021

(65) Prior Publication Data
US 2022/0032025 A1    Feb. 3, 2022

Related U.S. Application Data

(60) Provisional application No. 62/706,150, filed on Aug. 3, 2020.

(51) Int. Cl.
*A61M 35/00* (2006.01)
*A45D 34/04* (2006.01)
(Continued)

(52) U.S. Cl.
CPC .......... *A61M 35/003* (2013.01); *A45D 34/04* (2013.01); *A61B 5/0082* (2013.01); *A61B 5/103* (2013.01);
(Continued)

(58) Field of Classification Search
CPC ........ A61M 35/003; A61M 2205/3306; A61M 2205/52; A45D 34/04; A61B 5/0082;
(Continued)

(56) References Cited

U.S. PATENT DOCUMENTS

| 8,007,062 B2 | 8/2011 | Edgar et al. |
| 8,027,505 B2 | 9/2011 | Edgar et al. |

(Continued)

FOREIGN PATENT DOCUMENTS

| WO | WO 2007/022095 A1 | 2/2007 |
| WO | 2010/004565 A2 | 1/2010 |

(Continued)

OTHER PUBLICATIONS

International Search Report and Written Opinion dated Nov. 16, 2021 in corresponding International Application No. PCT/US2021/071079.

(Continued)

*Primary Examiner* — Kathleen Y Dulaney
(74) *Attorney, Agent, or Firm* — Wan Chieh Lee; Haug Partners LLP

(57) ABSTRACT

A device and method for selectively applying a composition to a treatment surface (e.g., skin) to alter an aesthetic appearance of the skin in the undereye region of the face. The device includes an applicator applying the composition to the skin, and a detector obtaining image data corresponding to an image of an area of skin. The device generates a target reflectance value based on the image data and past image data. The target reflectance value is higher than reflectance of at least half of areas corresponding to the image data and past image data. The device determines a desired level of reflectance modification for a location within the area of skin imaged by comparing image data corresponding to reflectance of the location to the target reflectance value, and directs the applicator to selectively apply the composition to the location based on the desired level of reflectance modification.

22 Claims, 7 Drawing Sheets

(51) Int. Cl.
*A61B 5/00* (2006.01)
*A61B 5/103* (2006.01)

(52) U.S. Cl.
CPC . *A61M 2205/3306* (2013.01); *A61M 2205/52* (2013.01)

(58) Field of Classification Search
CPC ..... A61B 5/103; A61B 5/0064; A61B 5/0088; A61B 5/441; A61B 5/0036; G06T 1/60
USPC ......................................................... 382/162
See application file for complete search history.

(56) References Cited

U.S. PATENT DOCUMENTS

| | | | |
|---|---|---|---|
| 8,103,061 B2 | 1/2012 | Payonk et al. | |
| 8,942,775 B2 | 1/2015 | Edgar et al. | |
| 9,020,184 B2 | 4/2015 | Edgar | |
| 9,247,802 B2 | 2/2016 | Edgar et al. | |
| 9,449,382 B2 | 9/2016 | Edgar et al. | |
| 9,462,872 B2 | 10/2016 | Edgar | |
| 10,010,155 B2* | 7/2018 | Ajiki | G06V 40/172 |
| 10,092,082 B2 | 10/2018 | Edgar et al. | |
| 10,405,795 B1* | 9/2019 | Osorio | A61B 5/1032 |
| 10,486,174 B2* | 11/2019 | Edgar | B41J 3/407 |
| 10,553,006 B2* | 2/2020 | Iglehart | G06F 3/04845 |
| 11,090,474 B2 | 8/2021 | Edgar | |
| 11,110,257 B2* | 9/2021 | Edgar | A61B 5/444 |
| 11,535,603 B1 | 12/2022 | DeWitt | |
| 2007/0035815 A1* | 2/2007 | Edgar | H04N 1/628 359/359 |
| 2008/0192999 A1 | 8/2008 | Edgar | |
| 2009/0025747 A1 | 1/2009 | Edgar et al. | |
| 2013/0302078 A1* | 11/2013 | Edgar | A61B 5/441 401/5 |
| 2016/0000209 A1* | 1/2016 | Yamanashi | G06T 11/00 600/300 |
| 2016/0107133 A1* | 4/2016 | Sugino | G01N 21/25 366/142 |
| 2017/0078584 A1 | 3/2017 | Won | |
| 2017/0256084 A1* | 9/2017 | Iglehart | G06V 40/16 |
| 2017/0340267 A1* | 11/2017 | Shen | G16H 40/67 |
| 2018/0126342 A1* | 5/2018 | Kent | A45D 34/042 |
| 2019/0080451 A1 | 3/2019 | Iglehart et al. | |
| 2019/0239752 A1* | 8/2019 | Dumitrescu | A61B 5/7264 |
| 2020/0107715 A1 | 4/2020 | Dana et al. | |
| 2022/0237811 A1* | 7/2022 | Cai | G06V 10/764 |
| 2022/0401514 A1 | 12/2022 | Such | |

FOREIGN PATENT DOCUMENTS

| | | |
|---|---|---|
| WO | 2010/145669 | 12/2010 |
| WO | 2012/103048 A2 | 8/2012 |
| WO | 2015/161009 A1 | 10/2015 |
| WO | 2015/191824 | 12/2015 |
| WO | WO 2020/139890 A1 | 7/2020 |

OTHER PUBLICATIONS

International Preliminary Report on Patentability dated Feb. 7, 2023 in corresponding International Application No. PCT/US2021/071079.

International Search Report and Written Opinion dated Mar. 23, 2022 in corresponding International Application No. PCT/US2021/061226.

* cited by examiner

SYSTEM AND METHOD FOR SELECTIVE APPLICATION OF COSMETIC COMPOSITION TO IMPART UNDEREYE BRIGHTENING

PRIORITY CLAIM

The present application claims priority to U.S. Provisional Application Ser. No. 62/706,150 filed Aug. 3, 2020, the entire contents of which is hereby incorporated by reference herein.

FIELD OF INVENTION

The present invention relates to devices and methods for selectively applying a composition onto a treatment surface, such as a keratinous surface, (e.g., the skin, hair, or nails), or enamel (e.g., teeth) of a user. More specifically, the invention relates to devices and methods for selectively applying a topical composition to reduce appearance of undesirable skin features in an undereye region and enhance the aesthetic appearance of skin.

BACKGROUND

A darkened appearance in an undereye region of a person's face may be associated with a reduced perception of beauty. The appearance of the undereye region is particularly sensitive to underlying physiological changes because the skin in this region is thin and flexible. The thin structure of skin in the undereye region allows for small physiological changes (e.g., changes to blood flow) in the region to impart visible changes to the appearance of the undereye region. For example, as a person becomes tired or ill, capillaries in the undereye region may dilate and impart a darkened appearance to the undereye region. This darkened appearance may be caused by stagnated blood in the capillaries that appears purple or blue, a buildup of dead blood cells in the capillaries that appears yellow, black or blue, which is analogous to coloration typically found in a bruise, and undesired in the aesthetic appearance of an undereye region of a person's face. Furthermore, as a person ages, the darkened appearance of the undereye region may expand into a larger area and the skin in the undereye region may also sag and merge with other darkened appearance of skin from other physiological regions on the face. The coloration of the undereye region can contribute significantly to the perceived aesthetic appearance of skin. Therefore, it is often desired to reduce darkened appearance of the undereye region to improve aesthetic appearance of the skin of the person's face.

SUMMARY OF THE INVENTION

One exemplary embodiment of the present invention is directed to a method for selectively applying a composition to skin within an undereye region of a user. The method comprises (a) obtaining, by a detector arrangement, image data corresponding to an image of an area of skin in the undereye region. The method also comprises (b) generating a target reflectance value based on the image data and past image data. The past image data correspond to images of a plurality of areas of skin previously imaged by the detector arrangement. The target reflectance value is higher than reflectance of at least half of the group consisting of the area of skin imaged in step (a), and the plurality of areas of skin previously imaged by the detector arrangement. The method further comprises (c) determining, by the processing arrangement, a desired level of reflectance modification for a location within the area of skin imaged in step (a) by comparing image data corresponding to reflectance of the location to the target reflectance value. The method further comprises (d) selectively applying, by an applicator arrangement, the composition to the location based on the desired level of reflectance modification.

In another aspect of the present application, a handheld device for selectively applying a composition to skin within an undereye region of a user is provided. The device comprises an applicator arrangement applying the composition to the skin within the undereye region and a detector arrangement obtaining image data corresponding to an image of an area of skin in the undereye region. The device further comprises a memory storage device storing past image data corresponding to images of a plurality of areas of skin previously imaged by the detector arrangement. The device further comprises a processor and a non-transitory computer readable storage medium including a set of instructions executable by the processor. The set of instructions operable to analyze the image data and past image data to generate a target reflectance value based on the image data and past image data, wherein the past image data correspond to images of a plurality of areas of skin previously imaged by the detector arrangement, wherein the target reflectance value is higher than reflectance of at least half of the group consisting of the area of skin imaged, and the plurality of areas of skin previously imaged by the detector arrangement, determine a desired level of reflectance modification for a location within the area of skin imaged by comparing image data corresponding to reflectance of the location to the target reflectance value, and direct the applicator arrangement to selectively apply the composition to the location based on the desired level of reflectance modification.

In a further aspect of the present application, another method for selectively applying a composition to skin within an undereye region of a user is provided. The method comprises obtaining, by a detector arrangement, image data corresponding to an image of an area of skin in the undereye region. The area of skin consisting of a plurality of skin frames imaged by the detector arrangement. The method also comprises analyzing, by a processing arrangement, the image data to generate a target reflectance value higher than reflectance of at least half of the plurality of skin frames imaged by the detector arrangement. The method further comprises determining, by the processing arrangement, a desired level of reflectance modification for a location within each of the plurality of frames by comparing image data corresponding to reflectance of the location to the target reflectance value. The method further comprises selectively applying, by an applicator arrangement, the composition to each location based on the corresponding desired level of reflectance modification determined for the location.

In another aspect of the present application, a handheld device for selectively applying a composition to skin within an undereye region of a user is provided. The device comprises a detector arrangement obtaining image data corresponding to an image of an area of skin in the undereye region. The area of skin consists of a plurality of skin frames imaged by the detector arrangement. The device also comprises an applicator arrangement comprising a plurality of nozzles applying the composition to the area of skin. Each of the plurality of nozzles is aligned to apply the composition to skin within a corresponding skin frame selected from the plurality of skin frames imaged by the detector arrangement. The device further comprises a processor and a non-transitory computer readable storage medium including a set of instructions executable by the processor. The set of instructions operable to analyze the image data to select a target frame from the plurality of skin frames, and to generate a target reflectance value based on image data corresponding to reflectance across the target frame, analyze the image data to generate a target reflectance value higher than reflectance of at least half of the plurality of skin frames imaged by the detector arrangement, determine a desired level of reflectance modification for a location within each of the plurality of frames by comparing image data corresponding to reflectance of the location to the target reflectance value, and direct the applicator arrangement to selectively apply the composition to each location based on the corresponding desired level of reflectance modification determined for the location.

These and other aspects of the invention will become apparent to those skilled in the art after a reading of the following detailed description of the invention, including the figures and appended claims.

DETAILED DESCRIPTION

The term "suitable for topical application" or "suitable for topical administration" as herein refers to those ingredients and/or treatments that are suitable for use on the skin, in particular, the skin of a human, without undue toxicity, incompatibility, instability, irritation, allergic response, unsightly visual appearance or the like.

The term "frexel" as used herein refers to a small pixel-like region of skin, which may correspond to a single large pixel or a small number of pixels in a digitally obtained image of the corresponding portion of skin. For example, a frexel may correspond to a skin area having an average diameter from about ⅟32 to about ¼ inch.

The term "opacity" as used herein refers to an amount of coverage a composition provides over a skin surface. If a composition is 100% opaque, the composition would completely cover the skin surface. If the composition is 0% opaque, the appearance of the skin would be that of the underlying skin and the composition would not be visible. If the composition is 50% opaque, then the appearance of the skin would be an equally weighted average of the composition and the underlying skin.

The present application provides a system, device and method for selectively applying a composition to skin in an undereye region of a face of a mammal or a human. More particularly, the present application provides a method, device and system for selectively applying a topical composition to the skin within an undereye region of the user to address darkened appearance of skin in the undereye region whose appearance the user wishes to minimize or eliminate to improve an overall aesthetic appearance of the face of the user. The device of the present application analyzes an image of an area of skin to identify locations to which the composition should be applied to alter the visual appearance of the skin within the undereye region, e.g., to reduce or eliminate appearance of artifacts on the skin such as dark, puffy and/or saggy circles in the undereye region. The composition may be a cosmetic composition and/or a skin treatment composition for improving the appearance and/or health of the skin in the undereye region.

Figure 1:
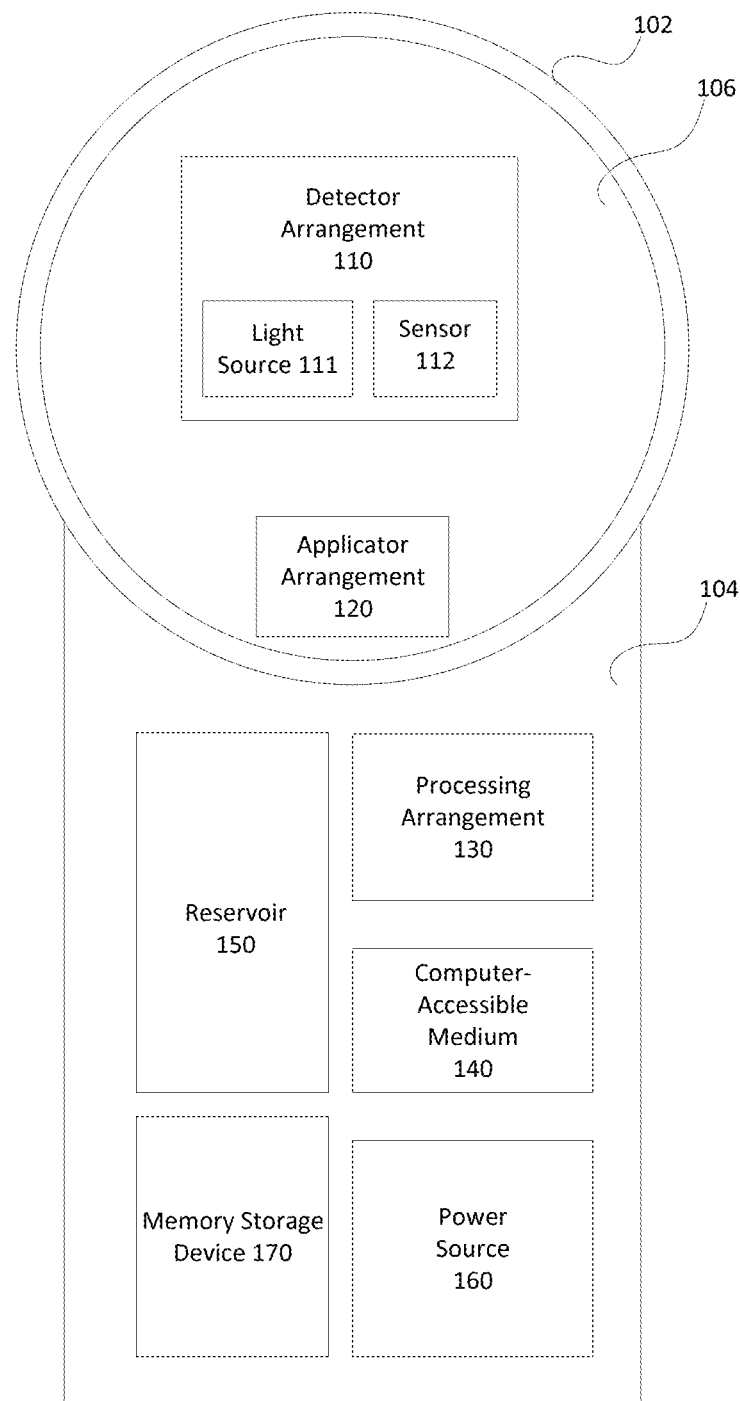
FIG. 1 shows a block diagram of an exemplary device for selectively applying a composition to the skin in an undereye region of a user, according to an exemplary embodiment of the present application.

FIG. 1 shows a block diagram of an exemplary device 100 for applying a topical composition to the skin in an undereye region of a face of a mammal or a human. In some embodiments, the device 100 may be suitable for applying a topical composition to any region of skin of the user, but may switch to an undereye application mode specifically for applying the topical composition to skin within the undereye region. The device 100 of this embodiment is sized and shaped to be a handheld device designed to be held within a palm of a user's hand. The device 100 according to this embodiment comprises a head portion 102 and a handle portion 104. The head portion 102 of the device 100 is sized and shaped to be held over skin in the undereye region. The handle portion 104 of the device 100 has an elongated shape defining a cavity for housing components therein. In some embodiments, the handle portion 104 is sized and shaped to be held within the palm of the user's hand. In other embodiments, the handle portion 104 is sized and shaped to be held by the fingertips of the user's hand.

The head portion 102 of the device 100 according to this embodiment comprises a detector arrangement 110 obtaining image data corresponding to an image of an area of skin in the undereye region. The head portion 102 of this embodiment also comprises an applicator arrangement 120 selectively applying the composition to portions of the skin in the undereye region as directed by a processing arrangement 130 based on image data from the detector arrangement 110. In some embodiments, the detector arrangement 110 and the applicator arrangement 120 are part of an inset portion 106 of the head portion 102 such that when the head portion 102 is placed over an area of skin to be treated, the inset portion 106 is not in contact with the skin.

The detector arrangement 110 comprises at least one light source 111 delivering light (e.g., visible light) to the area of skin in the undereye region, and at least one sensor 112 detecting light reflected from the area of the skin. The light source(s) 111 may comprise any suitable light emitting device for illuminating the area of skin, for example, one or more LEDs. The light source(s) 111 are selected and arranged to provide an amount of illumination over the area of skin sufficient to detect and/or measure reflectance of light by the skin. Preferably, the light source(s) 111, collectively, provide a substantially uniform distribution of light over the area of skin being imaged. In one exemplary embodiment, the light source(s) 111 comprise at least one light emitting device for providing a green light. In a specific example, the light source(s) 111 comprise at least one green LED. The sensor 112 may comprise any suitable components for detecting reflectance of light from the skin. For example, the sensor 112 may be sensitive to an amount of reflected light in one or more wavelengths. Suitable sensors 112 may include, for example, photographic or video cameras (which may include different types of camera lenses), photodiodes and/or phototransistors as would be understood by those skilled in the art. The sensor(s) 112 of the detector arrangement 110 may be an RGB camera which can detect light in red, green and/or blue channels of the camera.

The detector arrangement 110, including the light source(s) 111 and sensor(s) 112, is operably connected to a processing arrangement 130 to execute instructions stored on a computer-accessible medium 140. The processing arrangement 130 in this embodiment controls the light source(s) 111 and receives and analyzes imaging data received from the sensor(s) 112. It is contemplated that the processing arrangement 130 and the computer-accessible medium 140 may be positioned anywhere within or external to the device 100. In one embodiment, as shown in FIG. 1, the processing arrangement 130 and the computer-accessible medium 140 are located within the handle portion 104. The processing arrangement 130 in this embodiment also controls the applicator arrangement 120 to selectively apply the composition to desired frexels. The processing arrangement 130 may be, e.g., entirely or a part of, or include, but is not limited to, a computer/processor that can include, e.g., one or more microprocessors, and use instructions stored on a computer-accessible medium 140 (e.g., memory storage device). The computer-accessible medium 140 may, for example, be a non-transitory computer-accessible medium containing executable instructions therein. The device 100 may further include a memory storage device for storing past image data correspond to images of a plurality of areas of skin previously imaged by the detector arrangement 110.

The applicator arrangement 120 according to this embodiment comprises at least one suitable composition application device for depositing a topical composition (e.g., a cosmetic composition and/or a skin treatment composition) onto frexels. An exemplary topical composition application device in this embodiment includes, for example, a sprayer (e.g., an electronic sprayer or airbrush sprayer), a drop control device, or any other suitable application device for applying a composition in small drops to desired locations as would be understood by those skilled in the art. In one exemplary embodiment, the applicator arrangement 120 comprises a nozzle for depositing a pressurized liquid or viscous composition in the form of a pressurized mist onto the skin to form a thin layer of coverage at a desired location. The nozzle may be any suitable device for depositing a thin layer of the composition onto aimed locations on the skin. In one exemplary embodiment, the nozzle may comprise dual chambers with a first chamber holding the liquid or viscous composition and a second chamber containing a propellant (e.g., compressed air or nitrogen gas) applying a pressure to, but not mixed with the composition when a pulse of the composition is dispensed to a frexel. In another example, the nozzle comprises a first chamber holding the liquid or viscous composition and a second chamber containing a propellant to be mixed with the composition when the composition is dispensed to a desired location. Although two exemplary embodiments of the nozzle are described above, it is contemplated that the device of the present application may include any suitable nozzle for dispensing droplets of the composition under pressure as would be understood by those skilled in the art.

The applicator arrangement 120 is operably connected to a reservoir 150 containing a topical composition to be applied to the skin, such that the composition within the reservoir 150 can be transferred from the reservoir 150 to the applicator arrangement 120 for deposition onto the skin. In particular, the applicator arrangement 120 is fluidly connected by a series of conduits, valves, and/or pressure sources to the reservoir 150. It is contemplated that the reservoir 150 may be housed anywhere within the device 100. In one exemplary embodiment, as shown in FIG. 1, the reservoir 150 is housed within the handle portion 104 of the device 100. The composition within the reservoir 150 is transferred from the reservoir 150 to the applicator arrangement 120 for deposition of the composition. In some embodiments, the reservoir 150 is a removeable container that can be replaced upon exhaustion of the contents therein. For example, the reservoir 150 may be a pressurized canister containing the composition to be applied to the skin therein.

The composition to be applied to the skin may be any composition suitable for topical application to the skin of an undereye region of a face. The composition to be applied to the skin may comprise, for example, any suitable cosmetic ingredients for modifying an appearance of the skin, such as, for example, an opaque substance, a tinted cosmetic, or any other suitable compositions for enhancing the appearance of skin. The composition may also comprise ingredients such as a moisturizer for hydration, a carrier, or a benefit agent (e.g., a beneficial compound/composition/extract or an active ingredient) for treating and/or ameliorating a skin condition, e.g., acne, hyperpigmentation, eczema, hives, vitiligo, psoriasis, rosacea, warts, shingles, cold sore, pigmentation and tone, redness/oxidative skin stress, wrinkles, brightening, sagging/elasticity, etc. Exemplary embodiments of benefit agents that may be incorporated into the composition are further described below.

A non-limiting list of useful hydrating active benefit agents includes hyaluronic acid, and humectants. The hyaluronic acid may be linear, cross-linked, or a mixture of linear and cross-linked hyaluronic acid. It may be in a salt form, such as sodium hyaluronate. A humectant is a compound intended to increase the water content of the top layers of skin (e.g., hygroscopic compounds). Examples of suitable humectants include, but are not limited to, glycerin, sorbitol or trehalose or a salt or ester thereof.

A non-limiting list of useful benefit agents for acne includes benzoyl peroxide, retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid, sulfur, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

A non-limiting list of useful pigmentation active benefit agents includes resorcinols, such as niacinamide, 4-hexyl resorcinol, curcuminoids (such as Sabiwhite (Tetrahydrocurcumin), phytic acid, resveratrol, soybean *glycine soja* oil, gluconolactone, azelaic acid, and retinoids including retinol, retinal, retinoic acid, retinyl acetate, and retinyl palmitate, enzymes such as laccase, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like. Examples of suitable tyrosinase inhibitors include but, are not limited to, Vitamin C and its derivatives, Vitamin E and its derivatives, Kojic Acid, Arbutin, resorcinols, hydroquinone, Flavones e.g., Licorice flavanoids, Licorice root extract, Mulberry root extract, *Dioscorea* Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-to copherol, alpha-tocotrienol, beta-tocotrienol, gamma-tocotrienol, delta-to cotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol, phenylethyl resorcinol, 1-(2,4-dihydroxyphenyl)-3-(2, 4-dimethoxy-3-methylphenyl)-Propane and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative A non-limiting list of useful redness/antioxidant active benefit agents includes water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis and extracts of feverfew. By "extracts of feverfew," it is meant extracts of the plant "*Tanacetum parthenium*," One particularly suitable feverfew extract is commercially available as about 20% active feverfew.

A non-limiting list of useful wrinkle active benefit agents includes N-acetyl glucosamine, 2-dimethylaminoethanol, copper salts such as copper chloride, peptides like argireline, syn-ake and those containing copper, coenzyme Q10, dill, blackberry, princess tree, *Picia anomala*, and chicory, resorcinols, such as 4-hexyl resorcinol, curcuminoids and retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid.

A non-limiting list of useful brightening active benefit agents includes Vitamin C and its derivatives such as Ascorbic Acid 2-Glucoside, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid.

A non-limiting list of useful benefit agents for sagging skin includes blackberry extracts, cotinus extracts, feverfew extracts, extracts of Phyllanthus niruri and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

Additional skin benefit agents or actives may include those actives listed in the following paragraphs. While some of these actives may have been listed above, they are included below to ensure a more robust listing.

Examples of suitable additional benefit agents include: skin lightening agents, darkening agents, anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pHchanging agents, and the like. Examples of various suitable additional cosmetically acceptable actives include UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate 0 (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

Examples of suitable skin lightening benefit agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like.

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea* Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like.

Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like.

In some preferred embodiments, useful benefit agents for acne include, but are not limited, salicylic acid, Zinc PCA (Zinc Pyrrolidone carboxylic acid), Allantoin (5-ureido-hydantoin), Rosemary, 4-hexylresorcinol, N-acetyl glucosamine, gluconolactone, niacinamide, azelaic acid, and resveratrol.

In some preferred embodiments, a list of useful pigmentation active benefit agents includes tetrahydrocurcumin, phytic acid, resveratrol, soybean *glycine soja* oil, gluconolactone, laccase, 4-hexyl resorcinol, N-acetyl glucosamine, gluconolactone, niacinamide, azelaic acid, and resveratrol.

In some preferred embodiments, a list of useful active benefit agents includes to simultaneously treat acne and pigmentation includes 4-hexyl resorcinol, N-acetyl glucosamine, gluconolactone, niacinamide, azelaic acid, and resveratrol.

The composition may be a cosmetic composition (which may or may not include additional active ingredients for the treatment of skin) that is applied to the skin to alter or minimize the appearance of an artifact, in particular, appearance of darken skin in an undereye region of a face of a user, based on the image data supplied by the detector arrangement 110. In one particular embodiment, the composition comprises one or more reflectance modifying agents (RMAs) (any component useful for altering reflectance of the skin). For example, suitable RMAs may include inks, dyes, pigments, bleaching agents, chemically altering agents and other substances that may be used to alter the reflectance of the skin. Some suitable RMAs may include a transparent RMA, such as a dye or a diluted pigment. Other suitable RMAs may include an opaque RMA having high refractive index particles. In particular, the high refractive index particles may comprise particles having a refractive index of 2.0 or greater. In one specific example, the RMA may comprise particles of titanium dioxide. Specifically, the titanium dioxide particles may be uniformly distributed and/or suspended in the cosmetic composition.

The device 100 according to this embodiment further comprises a power source 160 for providing power to control and operate the device 100. It is contemplated that the power source 160 may be located anywhere within the device 100 or external to the device 100. In one exemplary embodiment, as shown in FIG. 1, the power source 160 which is housed within the handle portion 104 of the device 100 is operably connected to the detector arrangement 110, the applicator arrangement 120 and/or the processing arrangement 130. Those skilled in the art will understand that various known suitable sources of power may be used. For example, the power source 160 may comprise a battery or a connection to an external source of power. In particular, the power source 160 may comprise a rechargeable battery device.

In use, the head portion 102 is placed over an area of skin in the undereye region that is to be treated. During use, the device 100 may be utilized to image a plurality of different areas of skin. For example, the head portion 102 may be moved across a surface of the skin allowing the device 100 to continuously image (at any desired frame rate) different areas of the skin to obtain image data and analyze the image data to selectively apply the composition to desired frexels on the skin. More particularly, the user may move the head portion 102 back and forth across the surface of the skin in multiple passes to allow the device 100 to review previously treated areas to detect artifacts which were missed or incompletely addressed and apply the composition to identified artifacts on the skin.

Figure 2:
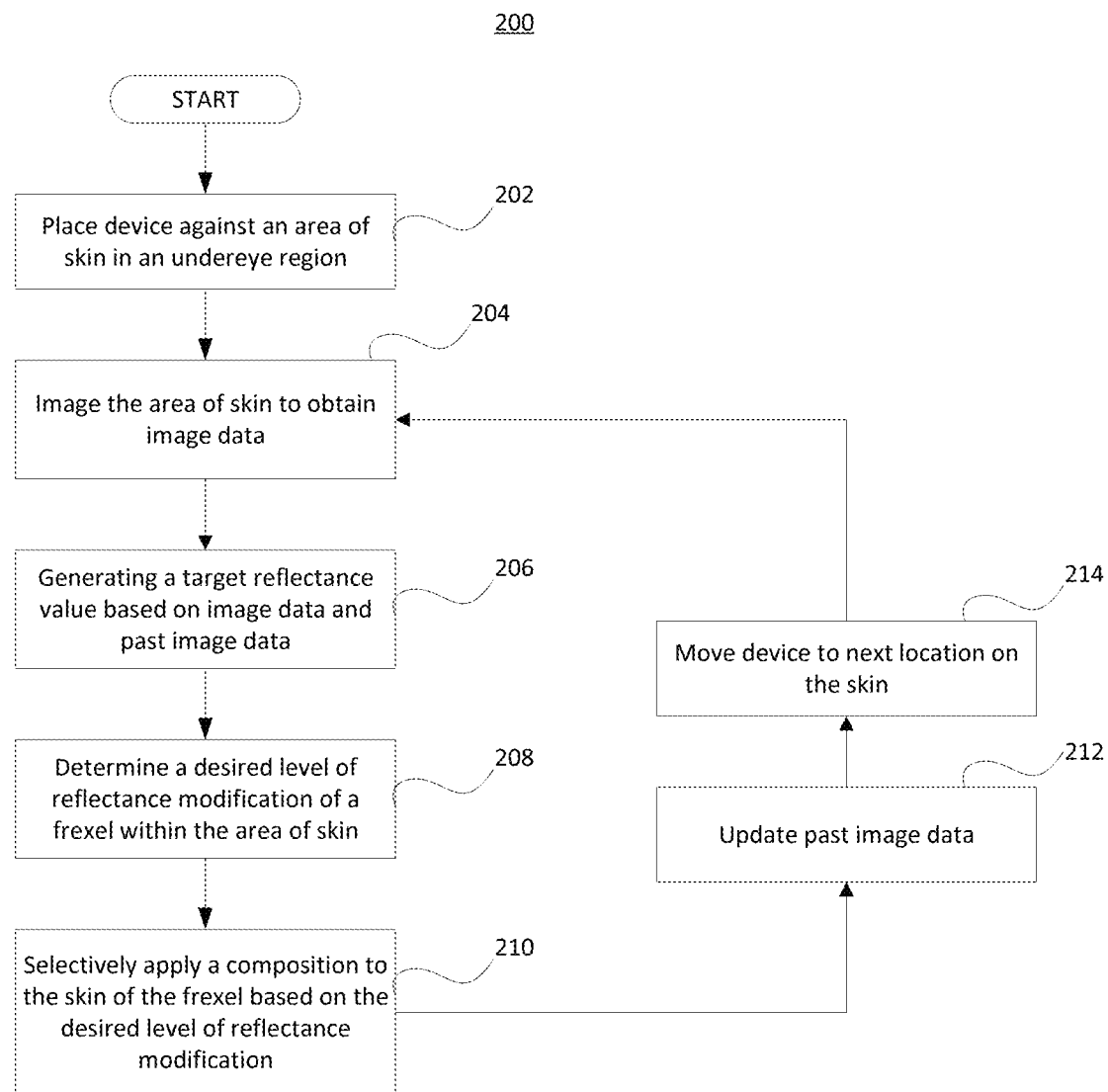
FIG. 2 shows an exemplary method for selectively applying a topical composition to the skin in an undereye region of a user, according to an exemplary embodiment of the present application.

The present application also includes a method for selectively applying a composition to skin within an undereye region of a face of a user. The undereye region may be an area of skin below the eyes of the user. In particular, the undereye region may be an area of skin that is within 50 mm, within 30 mm, or within 20 mm of the edges of the lower eyelids of the user. An exemplary method 200 is shown in FIG. 2. In step 202, the user may place a head portion 102 of the device 100 against a surface of skin in the undereye region. In step 204, the device 100 may sense and/or image the area of skin over which the device 100 is positioned to obtain image data. The area of skin may be in any suitable shape, such as, for example, square, circular, rectangular, etc.

In step 206, the device 100, in particular, the processing arrangement 130, analyzes the image data and past image data to generate a target reflectance value. The target reflectance value corresponds to a desired goal reflectance for improving aesthetic appearance of skin. The desired goal reflectance may correspond to a level of reflectance for unblemished skin and/or younger skin. The past image data corresponds to images of a plurality of areas of skin previously imaged by the detector arrangement 110. In particular, the past image data corresponds to images of a plurality of areas of skin within the undereye region that were previously imaged by the detector arrangement 110 within the same use session, as the head portion 102 was moved by the user back and forth across the surface of the skin in the undereye region in previous passes within the same use session. In some embodiments, the past image data corresponds to images of a plurality of areas of skin adjacent to the area of skin imaged in step 204. In other embodiments, the past image data corresponds to images of a plurality of areas of skin that are within a predetermined distance from the area of skin imaged in step 204. In further embodiments, the past image data corresponds to image of a plurality of areas of skin that were imaged immediately prior to the area of skin imaged in step 204. Specifically, the past image data may include a predetermined number of images of areas of skin that were imaged immediately prior to the area of skin imaged in step 204. The predetermined number of images may be from 1 to 25, or from 3 to 10. In one particular embodiment, the predetermined number of images is 4 or 5. The visual appearance of skin within the undereye region can include large artifacts e.g., dark, puffy and/or saggy circle, that may be aesthetically undesirable and to which a user may seek to modify. Therefore, the method 200 analyzes image data obtained from the area of skin imaged in step 204 as well as past image data so as to evaluate a larger skin surface in the undereye region before determining whether and how much of a modification to an aesthetic appearance of skin in the undereye region is desired.

The processing arrangement 130 generates a target reflectance value by analyzing the image data and past image data to determine a target reflectance value that is lighter (e.g., having a higher reflectance value) than at least half of the group consisting of the area of skin currently imaged (in step 204) and the plurality of areas of skin previously imaged by the device 100 corresponding to the past image data, as discussed above. In some embodiments, the target reflectance value is lighter than at least 70%, at least 75%, at least 80%, at least 90%, at least 95% or at least 99% of the group consisting of the reflectance values for the area of skin currently imaged and the plurality of areas of skin previously imaged corresponding to the past image data.

In one embodiment, the processing arrangement 130 first selects a target frame from the group consisting of the area of skin imaged in step 204 and the plurality of areas of skin previously imaged corresponding to the past image data, and generates a target reflectance value based on data corresponding to the target frame. The target frame may be selected as an area having a lighter reflectance than at least half of the group consisting of the area of skin currently imaged (in step 204) and the plurality of areas of skin corresponding to the past image data. In particular, the target frame may be an area having a reflectance value within an upper 1%, 5%, 10%, 20%, 25%, or 30% of the distribution of reflectance values for the group consisting of the area of skin currently imaged and the plurality of areas of skin previously imaged corresponding to the past image data. In one specific embodiment, the target frame may be an area having a lightest reflectance (e.g., highest reflectance value) selected from the group consisting of the area of skin currently imaged and the plurality of areas of skin previously imaged corresponding to the past image data. More particularly the processing arrangement 130 may analyze the image and the past image data to determine an average reflectance value for across each of: (1) the area of skin imaged in step 204, and (2) the plurality of areas of skin corresponding to the past image data. The processing arrangement 130 compares the average reflectance values of these areas of skin and identifies the target frame based on the criteria described above. The term "average" as used herein refers to any suitable representation of a set of values, and may be a linear average, mean, median, maximum, minimum or weighted average. In one exemplary embodiment, the average reflectance values of these area of skin are mean or median values.

In one exemplary embodiment, the target reflectance value is determined by the processing arrangement 130 as the reflectance of a frexel located at the center of the target frame. In other embodiments, the target reflectance value is determined by the processing arrangement 130 as an average reflectance of the frexels within the target frame. In another exemplary embodiment, the target reflectance value is a mean or median reflectance of the frexels within the target frame. In a further embodiment, the target reflectance is a weighted average reflectance value of the frexels within the target frame. For example, reflectance of frexels at or near a center of the location may be weighed more than reflectance of frexels at or near outer edges of the target frame to generate the target reflectance value as a weighted average of reflectance of the frexels across the target frame. In another embodiment, the target reflectance value may be a mean, a median or a minimum reflectance of the frexels within the target frame such that small skin artifacts, e.g., light hairs or freckles, within the undereye region are ignored by method 200.

In another embodiment, the processing arrangement 130 generates a target reflectance value by obtaining an average of the reflectance values of an upper 1%, 5%, 10%, 20%, 25%, or 30% of the distribution of reflectance values for the group consisting of the area of skin currently imaged and the plurality of areas of skin previously imaged corresponding to the past image data. For example, the processing arrangement 130 may generate a target reflectance value by obtaining a mean, a median, or a minimum of the reflectance values of an upper 1%, 5%, 10%, 20%, 25% or 30% of the distribution of reflectance values for the group consisting of the area of skin currently imaged and the plurality of areas of skin previously imaged corresponding to the past image data.

In step 208, the processing arrangement 130 analyzes the image data, determines reflectance of a location within the area of skin imaged in step 204, and compares the reflectance of the location to the target reflectance value to determine a desired level of reflectance modification for the location. The location may be an area of skin at an aimed location of the applicator arrangement 120 (i.e., a frexel or frexels to which a drop emitted from each composition applying nozzle of the applicator arrangement 120 would be applied in the current alignment of the device relative to the skin). In some embodiments, the reflectance of the location is determined, by the processing arrangement 130, as the reflectance of a frexel located at a center of the location. In other embodiments, the reflectance of the location is determined by the processing arrangement 130 as an average reflectance of the frexel(s) to which the composition would be applied by the applicator arrangement 120. Specifically, the reflectance of the location is determined by the processing arrangement 130 as a mean or median reflectance of the frexel(s) to which the composition would be applied by the applicator arrangement 120.

The desired level of reflectance modification may correspond to an amount of modification needed to alter the reflectance of the location to attain the target reflectance value at the location. If the target reflectance value is less than the reflectance of the location (i.e., the target frame is darker than the location), modification to the reflectance of the location may not be desired. However, if the target reflectance value is greater than the reflectance of the location (i.e., the target frame is lighter than the location), then a desired level of reflectance modification may be determined by the processing arrangement 130. For example, the desired level of reflectance may be a function of a difference between the target reflectance value and the reflectance of the location. In one exemplary embodiment, the device 100 may include a composition comprising an RMA. The desired level of reflectance may be determined by the processing arrangement as a target opacity of the composition, as follows:

$$\text{Target Opacity} = (R_{target} - R_{location})/(R_{composition} - R_{location}),$$

where $R_{target}$ is the target reflectance value as described above, $R_{location}$ is the reflectance of the location, and $R_{composition}$ is reflectance of the composition comprising the RMA. A composition has a known reflectance and therefore, a constant value for $R_{composition}$ that can be stored in the memory storage device 170 and retrievable by the processing arrangement 130 for determining the target opacity for a location.

In step 210, the applicator arrangement 120 selectively deposits a topical composition to the location. In one embodiment, the applicator arrangement 120 applies a fixed amount of the composition to the location when the desired level of reflectance modification is above a predetermined threshold value. For example, the applicator arrangement 120 may apply a fixed amount of the composition to the location when the reflectance of the location is less than 90%, less than 80% or less than 75% of the target reflectance value. In another example, the applicator arrangement 120 may apply a fixed amount of the composition, having a fixed opacity, to the location when the Target Opacity is greater than the fixed opacity. Alternatively, the applicator arrangement 120 may apply a fixed amount of the composition, having a fixed opacity, to the location when the fixed opacity is less than 90-100% of the Target Opacity, mores specifically, less than 95% to 99% of the Target Opacity. In a further example, the applicator arrangement 120 may deposit an amount of the composition corresponding to the Target Opacity.

In some embodiments, the applicator arrangement 120 may withhold from depositing the topical composition to the location, if the device 100 determines that the device 100, in particular, the applicator arrangement 120, is within a predetermined distance from the edges of the lower eyelids of the user (e.g., within about 3 mm to about 5 mm from the edges of the lower eyelids). It is believed that it may not be aesthetically desirable to apply the composition to the entirety of the undereye region of the face of the user. Rather, it may be desired that darkness within a predetermined distance from the eyes of the user be left untreated to improve aesthetic appearance of the user. A person's visual perception of aesthetically desirable looks is believed to be related to a perception of health, youth and/or vitality. Traditional cosmetics aim to fully cover the undereye region to enhance the aesthetic appearance of a user in order to improve perception of beauty. However, it is noted that in younger people, an area directly under the eye can have a darkened appearance and therefore, the presence of this darkened appearance may be associated with a perception of youth. Furthermore, by allowing a portion of the darkened appearance immediately under the eyes of the user to show through, this darken portion of skin increases visual contrast in the appearance of the user's facial features (e.g., the darkened undereye region as compared to the white of the eye). This increase in visual contrast can be accomplished without application of a darkening cosmetic composition (e.g., eye shadow, eyeliner, and/or mascara) to visually draw attention towards the eyes so that visual appearance of fainter proximal skin artifacts are less noticeable to an observer. It is believed that as people age, darkness in the undereye region expands and sags, and it is therefore, desirable to modify the appearance of the expanding darkened undereye region with application of a cosmetic composition. However, it is desired that the darkened appearance in the undereye region not be completely modified with application of a cosmetic composition. Rather, it may be desired that darkness within an immediate proximity to the edges of the lower eyelids (e.g., within about 3 mm to about 5 mm) remain visible to provide an appearance that is believed to mimic natural youth and/or vitality. Furthermore, leaving an area within an immediate proximity to the edges of the lower eyelids, without application of any cosmetic composition, reduces risk for accidental dispensing of the cosmetic composition to the eye, or the user accidentally rubbing the cosmetic composition into the eye after application.

In step 212, the processing arrangement 130 updates the past image data to include the image data obtained from step 204 for subsequent iterations of the method 200. In one embodiment, the processing arrangement 130 stores the image data from step 204 in the memory storage device 170 so that it is subsequently retrievable by the processing arrangement as past image data in a subsequent iteration of the method 200.

In step 214, the user may move the device 100 to a new area of the skin in the undereye region and method 200 returns to step 204 and images, analyzes and selectively applies topical composition, as determined by the device 100, to this new area of skin in the undereye region in the same manner described above. This movement to a new area of skin may be detected by the device 100 by any suitable means, such as, for example, an accelerometer or image analysis. It is noted that the method 200 may be interrupted and terminated by the user before any one of steps 202 through 214 by any suitable operation, such as, for example, removing the device 100 from the skin or switching off the device, in particular, the power source of the device.

The method 200 described above may be initiated manually by the user or may be automatically initiated by detecting placement of the device 100 near the undereye region of the face of the user. In some embodiments, the user may initiate method 200 by setting the device 100 in an undereye application mode to initiate the method 200. For example, the device 100 may include a toggle button that allows the user to manually set the device 100 into an undereye application mode.

Alternatively, the user may initiate use of the device 100 for applying a composition to skin within the undereye region by placing the head portion 102 against a surface of skin in the undereye region (as described above in step 202) and the device 100 determines that it is placed in the undereye region, without manual inputs from the user. If the device 100 determines that the device 100 has been placed in the undereye region, method 200 continues to step 204. Otherwise, method 200 is not applicable. In this embodiment, the device 100 may detect positioning of the device 100 at the undereye region by any suitable methods. For example, the device 100 may be positionally aware of placement of the device 100 relative to a face of the user. In another example, the device 100 may be positionally aware of placement of the device 100 relative to various markers corresponding to key positions on a face of the user. In a further example, the device 100 may be positionally aware of placement of the device 100 relative to various facial regions (e.g., eyelids, eyeballs, eyelashes, nose, cheeks, lips, etc.) on a face of the user. In a further example, the device 100 may generate a map and/or a composite image of a face of a user as the user moves the head portion 102 back and forth across the surface of the skin in multiple passes during use, and the device 100 may identify placement of the device 100 relative to the map and/or the composite image.

In another example, the device 100 may be used in a system in conjunction with an eye covering device. The user places an eye covering device over the eyes of the user's face before placing the device 100 against a surface of skin in the undereye region. The device 100 may automatically switch to an undereye application mode upon detecting that it is within close proximity to the eye covering device. In one exemplary embodiment, the eye covering device may include suitable marker(s), such as, for example, magnetic pellets or a metal frame at or near a lower edge of the eye covering device. The device 100 may further include a suitable detector (e.g., a magnetic detector) that is configured to detect proximity of the device 100 to the marker(s) of the eye covering device. Detectors may include magnetic detectors, induction sensors, capacitive sensors, optical sensors, ultrasonic sensors, Hall effect sensors, and/or any other suitable proximity sensors for detecting presence of a nearby object without physical contact as would be understood by those skilled in the art. In particular, the detector is an induction detector that is polarized to distinguish the eye covering device from the skin. The device 100 may initiate an undereye application mode when the detector determines that it is within a predetermined distance to the eye covering device. The device 100 may cease to operate in the undereye application mode when the detector determines that it is further than a threshold distance to the eye covering device, preferably, for at least a threshold amount of time. For example, the device 100 may be triggered to operate in an undereye application mode when the detector determines that it is within about 5 mm from the eye covering device and may decease to operate in the undereye application mode when the detector determines that the device 100 is further than about 15 mm from the eye covering device for more than 500 ms.

In another exemplary embodiment, the eye covering device may include a pattern or a grating at or near the lower edge of the eye covering device. The user may place the head portion 102 of the device 100 against a surface of skin in the undereye region (as described above in step 202) and the device 100 images the area of skin over which the device 100 is positioned to obtain image data (as described above in step 204). In this embodiment, the processing arrangement 130 analyzes the image data to determine if the pattern or grating at or near the lower edge of the eye covering device is detected within the imaged area. If the pattern or grating is detected, the device 100 automatically proceeds to step 206 to continue method 200 and operate in an undereye application mode.

The eye covering device is sized and shaped to be slim such that it covers from the edges of the lower eye lids to the upper eye lids. In some embodiments, the eye covering device is sized and shaped to cover the upper eye lids and an area of skin from the edges of the lower eye lids to about 3 to 5 mm away from the edge of the lower eye lids. When the eye covering device is placed over the eyes of the user, the eye covering device may be suitably sized such that darken appearance in an area of skin having a width of about 3 to 5 mm adjacent to the edges of the lower eye lids retain its natural coloring and is not modified by application of a topical composition from the device 100. By leaving this area of skin near the edges of the lower eye lids unmodified and therefore, retaining its natural darkened appearance, the overall aesthetic appearance of the skin of the face of the user may be improved. This small darkened area of skin may provide contrast so that other skin artifacts becomes less noticeable and/or impart an overall natural-looking aesthetic appearance of the skin.

In a further example, the device 100 is not used along with an eye covering device. Instead, the device 100 may be placed at or near a region of the eyes of the user (as described above in step 202) and the device 100 images the area of skin over which the device 100 is positioned to obtain image data (as described above in step 204). The processing arrangement 130 of this embodiment analyzes the image data to determine whether the device 100 is placed over an undereye region, and switches to an undereye application mode when the processing arrangement 130 determines that the device 100 is positioned in the undereye region. The processing arrangement 130 may analyze the image data to determine whether the device 100 is placed over facial features near the eyes of the user, such as, for example, lower eyelids, eyelashes, eyeballs, cheeks, area above the cheeks, etc. Upon detecting that the device 100 is placed against a surface of skin in the undereye region, the device 100 continues with method 200 and proceeds to step 206 to further analyze the image data as described above.

Figure 3:
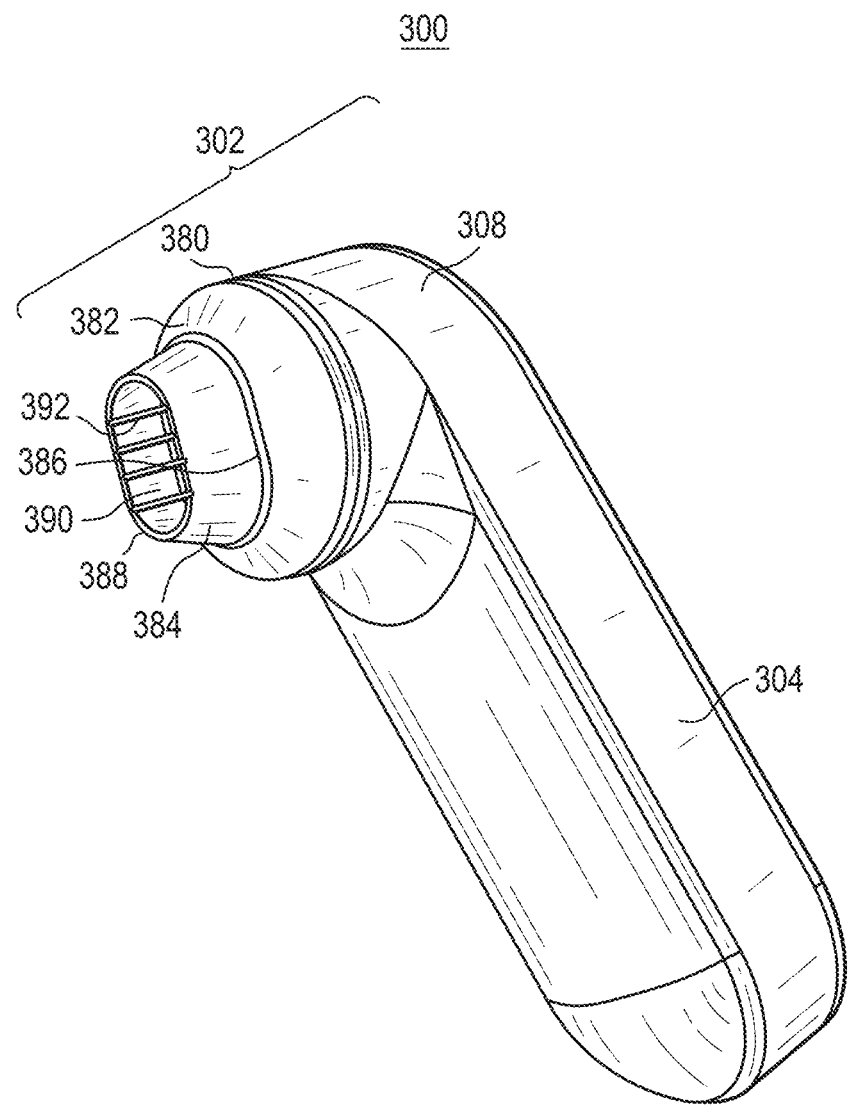
FIG. 3 shows an alternative device for selectively applying a composition to the skin in an undereye region of a user, according to another exemplary embodiment of the present application.

In an alternative embodiment, FIG. 3 shows another exemplary device 300 for applying a topical composition to the skin in an undereye region of a face of a mammal or a human is provided. The device 300 is similar to the device 100 described above, except as otherwise indicated below. In particular, the device 300 comprises a head portion 302 and a body portion 304. The body portion 304 is substantially similar to the body portion 104 of device 100, and includes a processing arrangement, a computer-accessible medium, a reservoir, a power source and a memory storage device similar to those discussed above with respect to device 100. The head portion 302 will be described further below.

The head portion 302 of the device 300 according to this embodiment comprises an end effector 380 that is reversibly attached to a body 308 of the head portion 302. The end effector 380 includes interior surfaces that define a cavity therein through which light can be delivered and an image of an area of skin in the undereye region can be captured by a detector arrangement. The end effector 380 comprises a base portion 382 that is reversibly attached to the body 308 and a protruding portion 384 that extends distally from the base portion 382. The protruding portion 384 of the end effector 380 extends from a proximal end 386 that is connected to the base portion 382 to a distal end 388 defining a distal opening 390 in the end effector 380. When the device 300 is in use, a distal end 388 of the protruding portion 384 is placed against skin of the undereye region and a detector arrangement (similar to detector arrangement 110 discussed above) is configured to image the skin of the undereye region to which the distal opening 390 is placed over. The area of skin over which the distal opening 390 is placed may consists of a plurality of frames of the skin of the undereye region, each frame being separately analyzed by a processing arrangement as discussed further below. Each frame of skin may have any suitable shape, such as, for example square, circular, rectangular, etc. In one exemplary embodiment, the area of skin over which the distal opening 390 is placed may consist of 1 to 25, or 3 to 10 frames of skin. In one particular embodiment, the area of skin over which the distal opening 390 is placed may consist of 4 or 5 frames of skin. As shown in FIG. 3, the distal end 388 of the protruding portion 384 has an elongate cross-sectional shape, such as an oval cross-sectional shape. In another exemplary embodiment, the distal end 398 of the protruding portion 384 has a rectangular cross-sectional shape.

In some embodiments, the plurality of skin frames may be arranged in a linear array along a length of the end effector 380. In particular, the distal end 388 of the protruding portion 384 includes a plurality of grating bars 392, extending across a width of the distal opening 390 of the end effector 380. The grating bars 392 divide the distal opening 390 of the end effector 380 into a plurality of distal opening segments. The distal opening segments may be arranged in a linear array along a length of the elongated effector where each of the distal opening segments may be placed over a corresponding frame of skin of the undereye region. The applicator arrangement of the device 300 includes at least one nozzle aligned to selectively apply a topical composition to each distal opening segment. Thus, each distal opening segment may be independently analyzed to identify portions of skin to which the topical composition is to be applied and, based on this analysis, operate the nozzles of the applicator arrangement associated with the corresponding segment. In some embodiments, the grating bars 392 are parallel or substantially parallel to one another. The plurality of grating bars 392 in this embodiment may also be spaced evenly or substantially evenly from one another.

Figure 4:
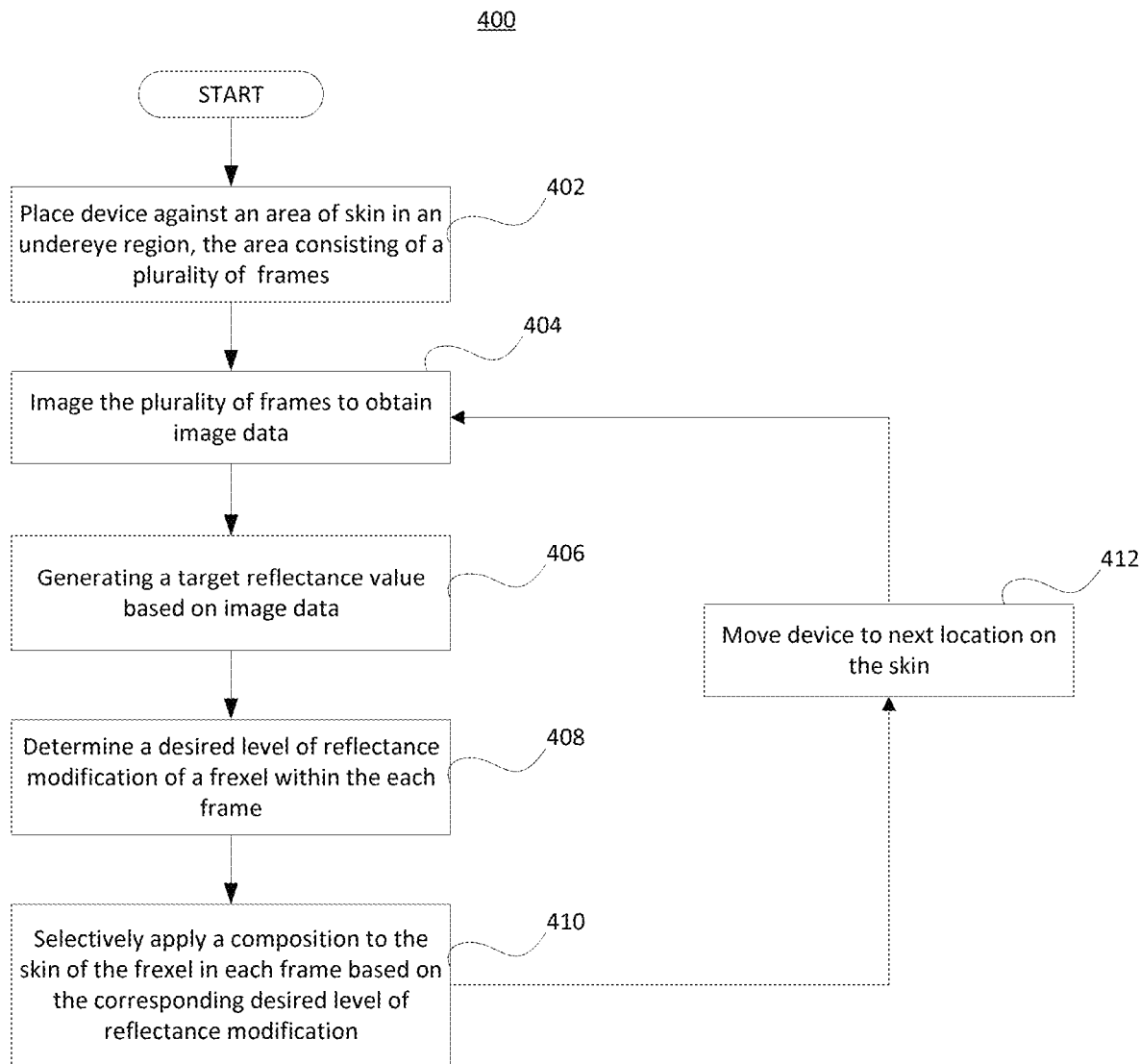
FIG. 4 shows an alternative exemplary method for selectively applying a topical composition to the skin in an undereye region of a user, according to another exemplary embodiment of the present application.

The device 300 may be used in an alternative embodiment of a method for selectively applying a composition to skin within an undereye region of a face of a user. An alternative exemplary method 400 is shown in FIG. 4. In step 402, the user may place a head portion 302 of the device 300 against a surface of skin in the undereye region, the area of skin consists of a plurality of skin frames imaged by the detector arrangement. In step 404, the device 300 senses and/or images the plurality of skin frames over which the device 300 is positioned to obtain image data for the plurality of skin frames. In step 406, the processing arrangement of the device 300 analyzes the image data to generate a target reflectance value that is lighter (e.g., having a higher reflectance value) than at least half of the plurality of frames imaged in step 404. In some embodiments, the target reflectance value is lighter than at least 70%, at least 75%, at least 80%, at least 90%, at least 95%, or at least 99% of the reflectance values of the plurality of frames.

In one embodiment, the processing arrangement of the device 300 analyzes the image data to select a target frame from the plurality of frames and generate a target reflectance value based on data corresponding to the target frame. The target frame may be selected as an area having a lighter reflectance than at least half of the plurality of frames. In particular, the target frame may be selected from a frame having a reflectance value within an upper 1%, 5%, 10%, 20%, 25% or 30% of the distribution of reflectance values for the plurality of frames. In one specific embodiment, the target frame may be a frame having the lightest reflectance (e.g., highest reflectance value) selected from the plurality of frames. More particularly, the processing arrangement may analyze the image data to determine an average reflectance value across each one of the plurality of frames and compare the average reflectance values of the plurality of frames to identify the target frame based on the criteria described above. In one exemplary embodiment, the average reflectance values of the plurality of frames are mean or median values. The target reflectance value is determined based on data corresponding to the target frame in the same way as discussed above with respect to step 206.

In another embodiment, the processing arrangement generates a target reflectance value by obtaining an average of the reflectance of an upper 1%, 5%, 10%, 20%, 25% or 30% of the distribution of reflectance values for the plurality of frames. For example, the processing arrangement may generate a target reflectance value by obtaining a mean, a median, or a minimum of the reflectance values of an upper 1%, 5%, 10%, 20%, 25% or 30% of the distribution of reflectance values for the plurality of frames.

In step 408, the processing arrangement of the device 300 analyzes the image data and determines reflectance of a location within each skin frame imaged in step 404 and compares the reflectance of each location to the target reflectance value to determine a desired level of reflectance modification for each location. Image data for each frame may be analyzed in a similar manner as described above in step 208.

In step 410, nozzles of the applicator arrangement are each independently controlled by the processing arrangement to selectively deposit a topical composition to a corresponding location in each corresponding skin frame. In one embodiment, each nozzle is configured to apply a fixed amount of the composition to a corresponding location in a corresponding skin frame based on the desired level of reflectance modification, the reflectance at the location and/or the target reflectance value, in a similar manner as discussed above in step 210.

Step 412 is similar to step 214 where the user moves the device 300 to a new area of skin and the method 400 returns to step 404 and images, analyzes and selectively applies topical composition, as determined by the device 300, to this new area of skin in the undereye region in the same manner for method 400 described above. Similar to method 200, the method 400 can also be interrupted and terminated by the user before any one of steps 402 through 412 by any suitable operation. The method 400 described above may also be initiated manually by the user or may be automatically initiated by detecting placement of the device 300 near the undereye region of the face of the user in a similar manner as described above with respect to method 200. The device 300 may also be used in conjunction with an eye covering device, as described above.

EXAMPLE

Example I

In Example I, an exemplary device 300 as described above and illustrated in FIG. 3 having an end effector 380 with a distal opening 390 having a rectangular shape is provided. When the device 300 is in use, it is placed against an area of skin in the undereye region consisting of a plurality of skin frames. Each of the skin frames being aligned in a linear array along a length of the end effector 380. In this example, the rectangular shape has a length of about 60 frexels and a width of about 30 frexels. Each of the frexels corresponds to a pixel for a sensor of the detector arrangement, specifically, a 150 dpi camera capturing an image of the skin. The camera is configured to image the plurality of skin frames over which the device 300 is positioned to obtain image data for the plurality of skin frames. In particular, the image data corresponds to image sensed in a green channel of the camera.

The natural coloration of the undereye region may appear to be bluer than skin at other regions of the face of the user. Therefore, a cosmetic composition for application to the undereye region may be formulated to have a color that is more biased towards a warm appearance to reduce the blue appearance of the undereye region. In Example I, the topical composition may comprise cosmetic ingredients having 10% more red pigmentation and 10% less blue pigmentation as compared to topical composition that would be used on skin for other regions of the face of the user.

Figure 5A:
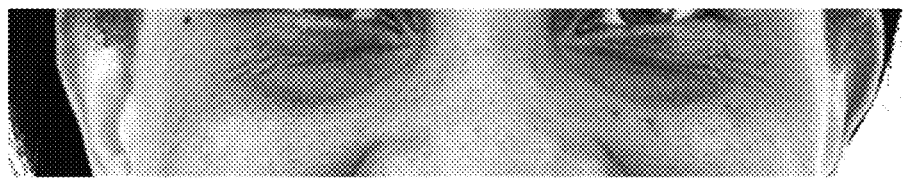
FIG. 5a shows an exemplary image of skin of an undereye region of an individual without application of a cosmetic composition.
Figure 5B:
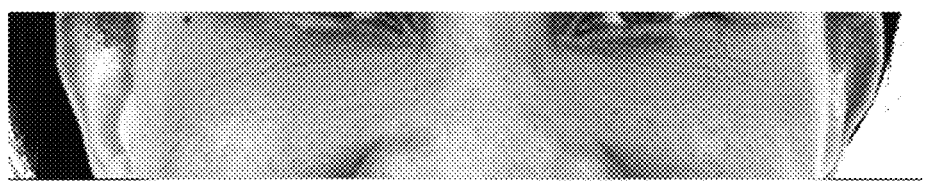
FIG. 5b shows the same region of skin of FIG. 5a with a simulated application of a cosmetic composition applied according to the exemplary embodiment of Example I.
Figure 5C:
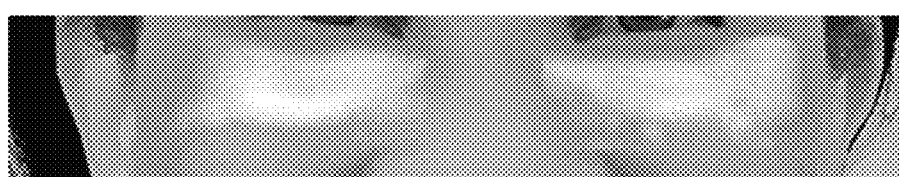
FIG. 5c shows a distribution of the composition simulated to be applied to the region of skin in FIG. 5b.
Figure 6A:
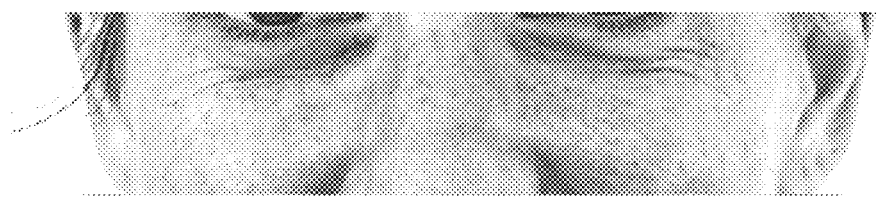
FIG. 6a shows an exemplary image of skin of an undereye region of another individual without application of a cosmetic composition
Figure 6B:
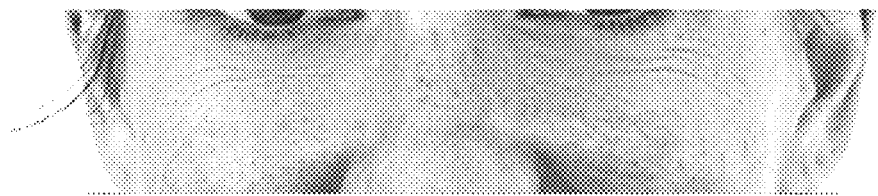
FIG. 6b shows the same region of skin of FIG. 6a with a simulated application of a cosmetic composition applied according to the exemplary embodiment of Example I.
Figure 6C:
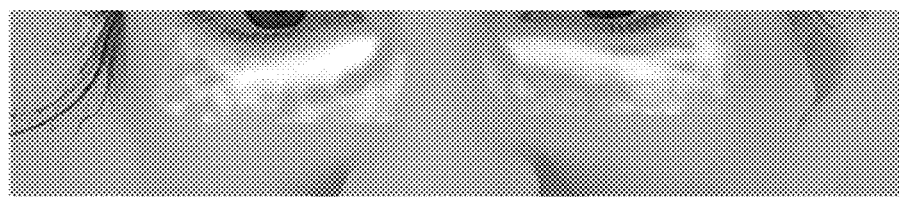
FIG. 6c shows a distribution of the composition simulated to be applied to the region of skin in FIG. 6b.
Figure 7A:
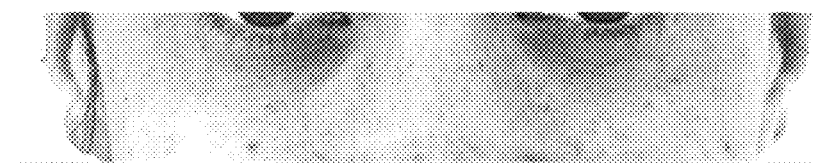
FIG. 7a shows an exemplary image of skin of an undereye region of another individual without application of a cosmetic composition.
Figure 7B:
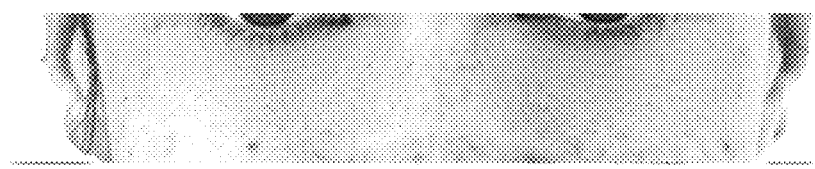
FIG. 7b shows the same region of skin of FIG. 7a with a simulated application of a cosmetic composition applied according to the exemplary embodiment of Example I.
Figure 7C:
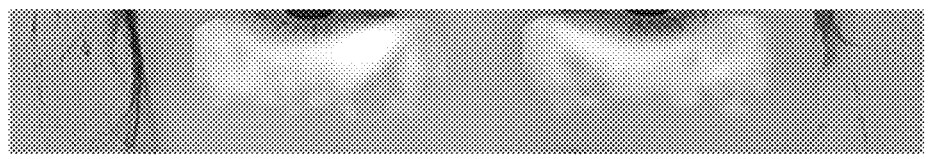
FIG. 7c shows a distribution of the composition simulated to be applied to the region of skin in FIG. 7b.
Figure 8A:
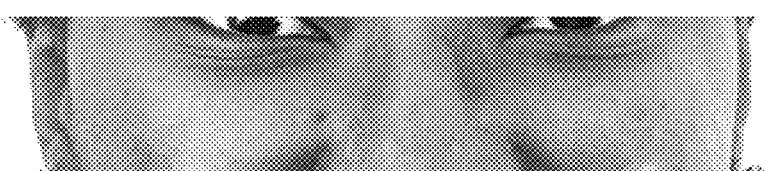
FIG. 8a shows an exemplary image of skin of an undereye region of another individual without application of a cosmetic composition.
Figure 8B:
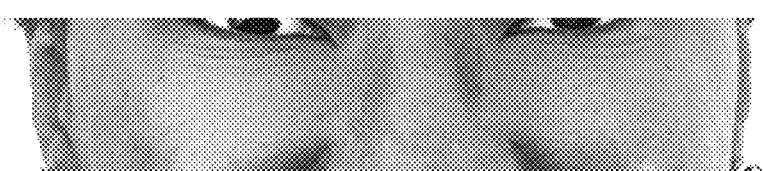
FIG. 8b shows the same region of skin of FIG. 8a with a simulated application of a cosmetic composition applied according to the exemplary embodiment of Example I.
Figure 8C:
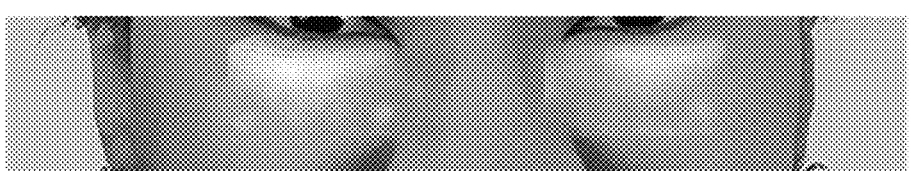
FIG. 8c shows a distribution of the composition simulated to be applied to the region of skin in FIG. 8b.
Figure 9A:
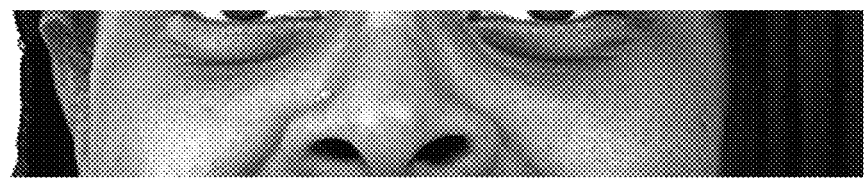
FIG. 9a shows an exemplary image of skin of an undereye region of another individual without application of a cosmetic composition.
Figure 9B:
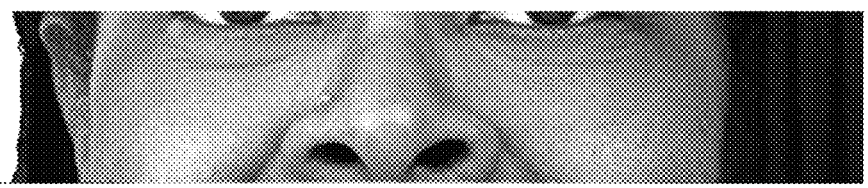
FIG. 9b shows the same region of skin of FIG. 9a with a simulated application of a cosmetic composition applied according to the exemplary embodiment of Example I.
Figure 9C:
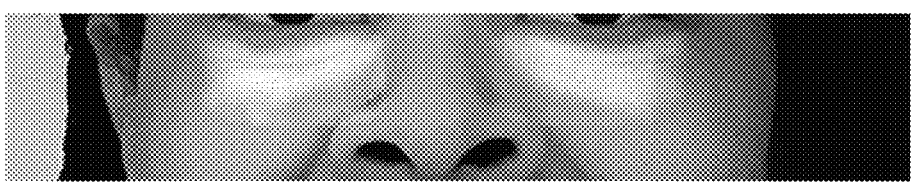
FIG. 9c shows a distribution of the composition simulated to be applied to the region of skin in FIG. 9b.

FIGS. 5a to 9c show exemplary images of skin of an undereye region of different individuals with and without simulated application of a cosmetic composition according to Example I, as captured in a green channel of a camera. FIG. 5a shows an exemplary image of skin of an undereye region of an individual without application of a cosmetic composition. FIG. 5b shows the same region of skin of FIG. 6a with a simulated application of a cosmetic composition applied in the manner described in Example I to an area of skin about 20 mm below the edges of the lower eye lids of the individual. FIG. 5c shows a distribution of the simulated application of the cosmetic composition of FIG. 5b. FIGS. 6a-6c, 7a-7c, 8a-8c, and 9a-9c show similar control and simulated application of a cosmetic composition as described above for FIGS. 5a-5c for three further individuals having different skin tones. FIGS. 6b, 7b, 8b and 9b show improvements in the aesthetic appearance of skin in the undereye region of these different individuals, which include both fair-skinned and dark-skinned individuals. Therefore, as shown in these simulated figures, Example I can be applied to improve aesthetic appearance of skin in the undereye region for different types of skin tones.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for selectively applying a composition to skin within an undereye region of a user, comprising:
   (a) obtaining, by a detector arrangement, image data corresponding to an image of an area of skin in the undereye region;
   (b) generating a target reflectance value based on the image data and past image data, wherein the past image data correspond to images of a plurality of areas of skin previously imaged by the detector arrangement, wherein the target reflectance value is higher than reflectance of at least half of the group consisting of the area of skin imaged in step (a), and the plurality of areas of skin previously imaged by the detector arrangement;
   (c) determining, by a processing arrangement, a desired level of reflectance modification for a location within the area of skin imaged in step (a) by comparing image data corresponding to reflectance of the location to the target reflectance value; and
   (d) selectively applying, by an applicator arrangement, the composition to the location based on the desired level of reflectance modification.

2. The method of claim 1, wherein the target reflectance value is higher than reflectance of at least 70%, at least 75%, at least 80%, at least 90%, at least 95% or at least 99% of the group consisting of the area of skin imaged in step (a), and the plurality of areas of skin previously imaged by the detector arrangement.

3. The method of claim 1, wherein the plurality of areas of skin of the past image data are adjacent to the area of skin imaged in step (a).

4. The method of claim 1, wherein the plurality of areas of skin of the past image data are within a predetermined distance from the area of skin imaged in step (a).

5. The method of claim 1, further comprising:
   (e) updating the past image data to include the image data corresponding to the area of skin imaged in step (a); and
   (f) repeating steps (a) through (d) for a further area of skin in the undereye region using the updated past image data.

6. The method of claim 5, wherein the plurality of areas of skin of the past image data consists of a predetermined number of areas imaged immediately prior to the area of skin imaged in step (a).

7. The method of claim 1, wherein the target reflectance value corresponds to an average reflectance across a target frame, the target frame is a frame selected from the group consisting of the area of skin imaged in step (a), and the plurality of areas of skin previously imaged by the detector arrangement.

8. The method of claim 7, wherein the target frame is selected by
   determining an average median reflectance value or a median reflectance value for each area of the group consisting of the area of skin imaged in step (a), and the plurality of areas of skin previously imaged by the detector arrangement,
   comparing the average median reflectance value or the median reflectance values for each area of the group consisting of the area of skin imaged in step (a), and the plurality of areas of skin previously imaged by the detector arrangement, and
   selecting as the target frame an area having a higher average reflectance value as compared to at least half of the group consisting of the area of skin imaged in step (a), and the plurality of areas of skin previously imaged by the detector arrangement.

9. The method of claim 8, wherein the target frame has a higher average reflectance value as compared to at least 70%, at least 75%, at least 80%, at least 90%, at least 95% or at least 99% of the group consisting of the area of skin imaged in step (a), and the plurality of areas of skin previously imaged by the detector arrangement.

10. The method of claim 1, wherein the applicator arrangement applies a fixed amount of the composition to the location when the desired level of reflectance modification is above a predetermined threshold value.

11. The method of claim 1, wherein the applicator arrangement applies an adjustable amount of the composition to the location, the adjustable amount being determined by the processing arrangement as a function of the desired level of reflectance modification.

12. The method of claim 1, wherein the composition is a cosmetic composition comprising a reflectance modifying agent.

13. The method of claim 12, wherein the composition comprises an active ingredient for treating a skin condition.

14. The method of claim 1, wherein the applicator arrangement withholds from applying the composition when the applicator arrangement is positioned within about 3 mm to about 5 mm from a lower edge of an eye of the user.

15. A handheld device for selectively applying a composition to skin within an undereye region of a user, comprising:
   an applicator arrangement applying the composition to the skin within the undereye region;
   a detector arrangement obtaining image data corresponding to an image of an area of skin in the undereye region;
   a memory storage device storing past image data corresponding to images of a plurality of areas of skin previously imaged by the detector arrangement; and
   a processor and a non-transitory computer readable storage medium including a set of instructions executable by the processor, the set of instructions operable to analyze the image data and past image data to generate a target reflectance value based on the image data and past image data, wherein the past image data correspond to images of a plurality of areas of skin previously imaged by the detector arrangement, wherein the target reflectance value is higher than reflectance of at least half of the group consisting of the area of skin imaged by the detector arrangement corresponding to the image data, and the plurality of areas of skin previously imaged by the detector arrangement corresponding to the past image data, determine a desired level of reflectance modification for a location within the area of skin imaged by the detector arrangement by comparing image data corresponding to reflectance of the location to the target reflectance value, and direct the applicator arrangement to selectively apply the composition to the location based on the desired level of reflectance modification.

16. The device of claim 15, wherein the set of instructions is further operable to update the past image data stored in the memory storage device to include the image data corresponding to the area of skin imaged, and repeat the above steps for a further area of skin in the undereye region using the updated past image data.

17. The device of claim 15, wherein the plurality of areas of skin of the past image data consists of a predetermined number of areas imaged immediately prior to the area of skin imaged by the detector arrangement corresponding to the image data.

18. The device of claim 15, wherein the target reflectance value corresponds to an average reflectance across the target frame or a median reflectance across the target frame.

19. The device of claim 15, wherein the processor directs the applicator arrangement to apply a fixed amount of the composition when the desired level of reflectance modification is above a predetermined threshold value.

20. The device of claim 15, wherein the processor directs the applicator arrangement to apply an adjustable amount of the composition to the location, the adjustable amount is determined by the processor as a function of the desired level of reflectance modification.

21. The device of claim 15, wherein the composition is a cosmetic composition comprising a reflectance modifying agent.

22. The device of claim 21, wherein the composition comprises an active ingredient for treating a skin condition.

* * * * *